United States Patent [19]

Grove, deceased

[11] 4,319,917

[45] Mar. 16, 1982

[54] N-(2-CYANOALKOXY)METHYL-N-(2-,3-, OR 6-ALKYLPHENYL)-α-HALOACETAMIDES

[75] Inventor: William S. Grove, deceased, late of Doylestown, Ohio, by Louise A. Grove, administratrix

[73] Assignee: PPG Industries, Inc., Pittsburgh, Pa.

[21] Appl. No.: 243,005

[22] Filed: Mar. 12, 1981

[51] Int. Cl.$^3$ .................... A01N 37/34; C07C 121/78
[52] U.S. Cl. .................... 71/105; 260/465 D
[58] Field of Search .................... 260/465 D; 71/105

[56] References Cited

U.S. PATENT DOCUMENTS

| | | | |
|---|---|---|---|
| 3,442,945 | 5/1969 | Olin | 260/562 |
| 3,965,139 | 6/1976 | Scozzie | 260/465 |
| 3,976,471 | 8/1976 | Richter et al. | 71/105 |
| 4,070,179 | 1/1978 | Vogel et al. | 260/562 |

*Primary Examiner*—Dolph H. Torrence
*Attorney, Agent, or Firm*—Edward J. Whitfield

[57] ABSTRACT

Disclosed are certain N-(2-cyanoalkoxy)methyl-N-(2-,3-, or 6-alkylphenyl)-α-haloacetamides having herbicidal activity, their mode of preparation and the use thereof to control weeds.

7 Claims, No Drawings

N-(2-CYANOALKOXY)METHYL-N-(2-,3-, OR 6-ALKYLPHENYL)-α-HALOACETAMIDES

FIELD OF THE INVENTION

This invention relates to N-(2-cyanoalkoxy)methyl-N-(2-, 3- or 6-alkylphenyl)-α-haloacetamides having herbicidal activity, the preparation thereof and the control of weeds therewith.

DESCRIPTION OF THE INVENTION

This invention relates to herbicidally active N-(2-cyanoalkoxy)methyl-N-(2-, 3- or 6-alkylphenyl)-α-haloacetamide compounds represented by the formula:

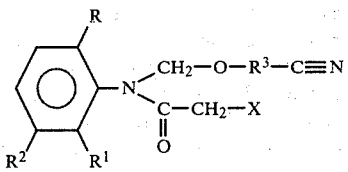

wherein:
R is alkyl containing 1 to 4 carbon atoms;
$R^1$ is hydrogen or alkyl containing 1 to 4 carbon atoms;
$R^2$ is hydrogen or alkyl containing 1 to 4 carbon atoms;
$R^3$ is alkylene containing 1 to 3 carbon atoms which may be monosubstituted by alkyl containing 1 to 3 carbon atoms: and
X is halogen.

Some examples of alkyl groups of which R, $R^1$ and $R^2$ are representative include methyl, ethyl, n-propyl, isopropyl, n-butyl, isobutyl or t-butyl. Methylene, ethylene or n-propylene are exemplary of alkylene groups represented by $R^3$. Suitable halogens represented by X include chlorine, bromine or iodine, preferably chlorine or bromine. Those compounds wherein R and $R^1$ are methyl or ethyl, $R^2$ is hydrogen, $R^3$ is an ethylene radical and X is chlorine are particularly preferred.

Although any compound within the scope of the above formula is believed to exhibit herbicidal activity in accordance with this invention, the compounds, N-(2-cyanoethoxy)methyl-N-(2-ethyl-6-methylphenyl)-α-chloroacetamide, N-(2-cyanoethoxy)methyl-N-(2,6-dimethylphenyl)-α-chloroacetamide and N-(2-cyanoethoxy)methyl-N-(2,6-diethylphenyl)-α-chloroacetamide have been found to be especially efficacious.

It is of course to be understood that the stereo and optical isomers of compounds represented by the above formula are within the scope of this invention.

The compounds of this invention are typically synthesized using conventional techniques by reacting an appropriately substituted aniline with haloacetyl halide in the presence of an acid acceptor, e.g. triethylamine to prepare the corresponding α-haloacetamide. The α-haloacetamide is then reacted with paraformaldehyde and hydrogen chloride, under anhydrous conditions to form the N-halomethyl-N-(2-, 3-, or 6-alkylphenyl)-α-haloacetamide of the formula

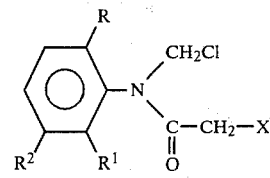

wherein R, $R^1$, $R^2$ and X are as previously defined. The N-halomethyl-N-(2-, 3-, or 6-alkylphenyl)-α-haloacetamide is then reacted with an appropriate hydroxyalkanenitrile of the formula, $OH-R^3C\equiv N$, wherein $R^3$ is as previously defined in the presence of an acid acceptor to form a compound of the invention. The above described reactions may of course, and preferably are, conducted in the presence of an inert organic solvent such as, for example, heptane, benzene, methylene chloride, dimethylformamide or the like. The starting materials may be obtained from commercial sources or prepared by known techniques.

Alternatively the compounds of this invention may be prepared by reacting the appropriately substituted aniline with paraformaldehyde in the first stage, followed by successive reaction with haloacetyl halide and hydroxyalkanenitrile, again employing conventional syntheses methods.

The following examples are illustrative of the preparation of certain specific compounds of this invention.

EXAMPLE I

Preparation of N-(2-cyanoethoxy)methyl-N-(2-ethyl-6-methylphenyl)-α-chloroacetamide (a) A 500-milliliter flask provided with a Dean-Stark trap and a magnetic stirring bar was charged with 27 grams (0.2 mole) of 6-ethyl-o-toluidine and 6 grams (0.2 mole) of paraformaldehyde in 350 milliliters of heptane. The stirred mixture was brought to reflux and water was removed azeotropically. After 4 hours at reflux, the mixture was cooled and filtered and the filtrate was concentrated on a rotary evaporator at 55° C. leaving a brown liquid residue. The residue was transferred to a distillation flask and fractionated through a micro column at 2 millimeters of mercury pressure. A 10 gram forecut was collected and discarded followed by a 12 gram fraction of N-methylidene-6-ethyl-o-toluidene.

(b) To a 100-milliliter flask provided with a reflux condenser, an addition funnel and a magnetic stirring bar was charged 4.41 grams (0.03 mole) of N-methylidene-6-ethyl-o-toluidene, prepared as described in paragraph (a), in 50 milliliters of benzene. To this solution was added dropwise 3.39 grams (0.03 mole) of a chloroacetyl chloride. An exothermic reaction was observed. After addition was complete, the mixture was heated to reflux and maintained at reflux for 3 hours. While at reflux, 6.06 grams (0.06 mole) of triethylamine and 2.13 grams (0.03 mole) of 3-hydroxypropionitrile were slowly added, after which additions the reaction mixture was continued at reflux. After a total reflux period of 20 hours the reaction mixture was cooled, transferred to a separatory funnel and washed consecutively with 40 milliliter portions of 1 Normal hydrochloric acid, 0.1 Normal sodium hydroxide and water. The organic layer was removed, dried over magnesium sulfate and concentrated on a rotary evaporator at 55° C. yielding 2.9 grams of a syrupy amber liquid identified by NMR spectroscopy as N-(2-cyanoethoxy)methyl-N-(2-ethyl-6-methylphenyl)-α-chloroacetamide.

EXAMPLE II

Preparation of
N-(2-cyanoethoxy)methyl-N-(2,6-dimethylphenyl)-α-chloroacetamide (a) To a 3-necked, 1-liter flask provided with a reflux condenser, an additional funnel and a magnetic stirring bar was charged 36.3 grams (0.3 mole) of 2,6-dimethyl aniline and 30.36 grams (0.3 mole) of triethylamine in 550 milliliters of methylene chloride. To the stirred solution, maintained at 0° to 5° C. by means of an ice bath, was added dropwise, over a period of 30 minutes, 33.9 grams (0.3 mole) of chloroacetyl chloride. The reaction mixture was then stirred at ambient temperature for 21 hours after which it was transferred to a separatory funnel and washed consecutively with 300 milliliter portions of 1 Normal hydrochloride acid, 10 percent aqueous sodium carbonate solution and water. The organic layer was removed, dried over magnesium sulfate and concentrated on a rotary evaporator at 55° C. leaving a bluish-gray solid. This solid was recrystallized from a hot 20:80 volume/volume ethylacetate-ligroin solution yielding 41 grams of gray, solid N-(2,6-dimethylphenyl)-α-chloroacetamide.

(b) To a 3-necked, 500 milliliter flask provided with a reflux condenser, a thermometer, a gas inlet tube, a drying tube and a magnetic stirring bar were charged 19.7 grams (0.1 mole) of the N-(2,6-dimethylphenyl)-α-chloroacetamide, prepared as described in paragraph (a), 4.5 grams (0.15 mole) of paraformaldehyde and 1.0 gram of anhydrous sodium sulfate in 250 milliliters of benzene. The mixture was vigorously stirred with heating at 50° C. and anhydrous gaseous hydrogen chloride was slowly bubbled into the mixture over a 5-hour period. An additional 10 grams of sodium sulfate was added, the mixture was stirred for an additional hour at 50° C., after which it was cooled and filtered. The filtrate was concentrated on a rotary evaporator at 55° C. leaving a semi-solid residue. The residue was vigorously swirled with 150 milliliters of benzene and petroleum ether was slowly added while swirling until the residue became pasty. The mixture was filtered and the filtrate concentrated on a rotary evaporator at 55° C. yielding 15.1 grams of a clear light brown liquid of N)-(chloromethyl)-N-(2,6-dimethylphenyl)-α-chloroacetamide.

(c) To a 3-necked, 100-milliliter flask provided with a reflux condenser, an addition funnel and a magnetic stirring bar were charged 4.9 grams (0.02 mole) of the N-(chloromethyl)-N-(2,6-dimethylphenyl)-α-chloroacetamide, prepared as described in paragraph (b), and 1.5 grams (0.022 mole) of 3-hydroxypropionitrile in 50 milliliters of benzene. To this stirred mixture, at ambient temperature, was added 2.02 grams (0.02 mole) of triethylamine. The mixture was then brought to reflux and maintained at reflux for 20 hours, after which it was cooled, transferred to a separatory funnel and washed consecutively with 30 milliliter portions of 1 Normal hydrochloric acid, water, 10 percent aqueous potassium carbonate solution and water. The organic layer was removed, dried over magnesium sulfate and concentrated on a rotary evaporator at 55° C. yielding 5.0 grams of a light brown syrupy liquid identified by NMR spectroscopy as N-(2-cyanoethoxy)methyl-N-(2,6-dimethylphenyl)-α-chloroacetamide.

EXAMPLE III

Preparation of
N-(2-cyanoethoxy)methyl-N-(2,6-diethylphenyl)-α-chloroacetamide (a) To a 3-necked, 1-liter flask provided with a reflux condenser, and addition funnel and a magnetic stirring bar were charged 44.7 grams (0.3 mole) of 2,6-diethylaniline and 30.36 grams (0.3 mole) of triethylamine in 600 milliliters of methylene chloride. To the stirred solution, maintained at 0° to 5° C. by means of an ice bath, was added dropwise, over a period of 30 minutes, 33.9 grams (0.3 mole) of chloroacetyl chloride. The reaction mixture was then stirred, at ambient temperature, for 5.5 hours after which it was transferred to a separatory funnel and washed consecutively with 200 milliliter portions of 1 Normal hydrochloric acid, water, 1 Normal sodium hydroxide and water. The organic layer was removed, dried over magnesium sulfate and concentrated on a rotary evaporator at 55° C. leaving a dark solid residue. This solid was recrystallized from a hot 20:80 volume/volume ethylacetate-ligroin solution yielding 51 grams of gray solid N-(2,6-diethylphenyl)-α-chloroacetamide.

(b) To a one-liter flask provided with a mechanical stirrer, a gas inlet tube, a Dean-Stark trap, a thermometer and a drying tube was charged 45 grams (0.2 mole) of N-(2,6-diethylphenyl)-α-chloroacetamide, prepared as described in paragraph (a), in 350 milliliters of anhydrous benzene. To this stirred solution was added 9 grams (0.3 mole) of paraformaldehyde and 20 grams of anhydrous sodium sulfate. The stirred mixture was brought to reflux and anhydrous, gaseous hydrogen chloride was slowly bubbled into the refluxing mixture, the water formed being azetropically removed. After 5 hours, hydrogen chloride addition was discontinued, an additional 20 grams of sodium sulfate were added and refluxing was continued. After a total reflux period of 65 hours, the mixture was cooled, filtered and concentrated on a rotary evaporator at 55° C. leaving a residue of a white solid suspended in a brown syrupy liquid. This residue was vigorously swirled with 30 milliliters of benzene. To the mixture was added 100 milliliters of petroleum ether resulting in the precipitation of the white solid which was removed by filtration. The filtrate was concentrated on a rotary evaporator at 55° C. leaving a solid-free brown liquid of N-(chloromethyl)-N-(2,6-diethylphenyl)-α-chloroacetamide.

(c) To a 3-necked, 100-milliliter flask provided with a reflux condenser, a thermometer, a gas inlet tube, a drying tube and a magnetic stirrer was charged 5.48 grams (0.02 mole) of N-(chloromethyl)-N-(2,6-diethylphenyl)-α-chloroacetamide, prepared as described in paragraph (b), in 50 milliliters of benzene. To this stirred solution was added 1.62 grams (0.0227 mole) of 3-hydroxypropionitrile followed by dropwise addition of 2.02 grams (0.02 mole) of triethylamine. The mixture was then brought to reflux and maintained at reflux for 20 hours, after which it was cooled, transferred to a separatory funnel and washed consecutively with 30 milliliter portions of 1 Normal hydrochloric acid, water, 10 percent aqueous potassium carbonate solution and water. The organic layer was removed, dried over magnesium sulfate and concentrated on a rotary evaporator at 55° C. yielding 3.88 grams of a light amber liquid identified by NMR spectroscopy as N-(2-cyanoethoxy)methyl-N-(2,6-diethylphenyl)-α-chloroacetamide.

The mode of synthesis of specific compounds of this invention have been illustrated in some detail by the foregoing Examples, but it is to be understood that any compound contemplated to be within the scope of this invention may be prepared by those skilled in the art simply by varying the choice of starting materials and using the illustrated technique or other suitable techniques.

The compounds of this invention are effective in regulating the growth of a variety of undesirable plants, i.e. weeds, when applied, in herbicidally effective amount, to the growth medium preferably prior to emergence of the weeds or alternatively to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be required. Of course, the efficacy of a particular compound against a particular weed species may readily be determined by straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, safeners, fertilizers, and the like. The compounds of this invention, whether or not in formulation with other agronomically acceptable materials, are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically such formulations will contain from about 5 to about 75 percent by weight of compound or compounds of this invention.

The compounds of this invention have been found effective in controlling a variety of broadleaf and grassy weeds at application rates of two pounds per acre or less preemergence. Exemplary of broadleaf weeds that may be effectively controlled by application of compounds of this invention are teaweed (*Sida spinosa*); jimsonweed (*Datura stramonium*); wild mustard (*Brassica caber*); and coffeeweed (*Daubentonia punicea*). For example, when the compound prepared according to Example I was tested for preemergence herbicidal activity against the above-mentioned broadleaf weed species under controlled laboratory conditions of light, temperature and humidity all of the weeds were either dead or injured beyond recovery within 19 days following application of the compound at a rate of two pounds per acre. Exemplary of grassy weeds that may be effectively controlled by application of compounds of this invention are wild oats (*Arena fatua*); yellow foxtail (*Setaria glauca*); large crabgrass (*Digitaria sanguinalis*); johnsongrass (*Sorghum halepense*); barnyardgrass (*Echinchloa crusgalli*); and yellow nutsedge (*Cyperus esculentus*); particularly the latter, which is a very difficult weed to control. For example, when the compounds prepared according to Examples I through III were individually tested for preemergence herbicidal activity against the above mentioned grassy weed species, under controlled laboratory conditions of light, temperature and humidity all of the weeds were either dead or injured beyond recovery within 19 days following application of the respective compounds at a rate of one pound per acre.

In addition, the compounds of this invention have been found to not cause significant damage to crops such as cotton, soybeans, tomatoes, corn and wheat, when applied in herbicidally effective amount, e.g. two pounds per acre, or less.

Although the invention has been described with reference to illustrative embodiments thereof, it is to be understood that it is not intended to be so limited, since many variations may be made therein by those skilled in the art without departing from the spirit and scope thereof, except as defined by the appended claims.

I claim:

1. A compound represented by the formula:

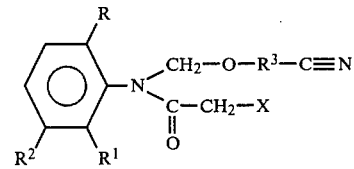

wherein:
R is alkyl containing 1 to 4 carbon atoms;
$R^1$ is hydrogen or alkyl containing 1 to 4 carbon atoms;
$R^2$ is hydrogen or alkyl containing 1 to 4 carbon atoms;
$R^3$ is alkylene containing 1 to 3 carbon atoms which may be monosubstituted by alkyl containing 1 to 3 carbon atoms; and
X is halogen.

2. A compound of claim 1 wherein R and $R^1$ are the same or different alkyl and $R^2$ is hydrogen.

3. A compound of claim 2 wherein R and $R^1$ are methyl or ethyl.

4. A compound of claim 1 wherein X is bromine or chlorine.

5. A compound of claim 1 selected from N-(2-cyanoethoxy)methyl-N-(2-ethyl-6-methylphenyl)-α-chloroacetamide; N-(2-cyanoethoxy)methyl-N-(2,6-dimethylphenyl)-α-chloroacetamide; or N-(2-cyanoethoxy)methyl-N-(2,6-diethylphenyl)-α-chloroacetamide.

6. A herbicidal composition containing a herbicidally effective amount of a compound or mixture of compounds defined in claim 1.

7. In a method of controlling weeds wherein a herbicidally effective amount of herbicide is applied to the growth medium prior to emergence of weeds therefrom wherein the improvement resides in using as the herbicide a herbicidally effective amount of a compound or mixture of compounds defined in claim 1.

* * * * *